(12) United States Patent  
Pohlman et al.

(10) Patent No.: US 9,125,416 B2  
(45) Date of Patent: Sep. 8, 2015

(54) PESTICIDAL MIXTURES

(75) Inventors: Matthias Pohlman, Freinsheim (DE); Markus Gewehr, Kastellaun (DE); Tatjana Sikuljak, Mannheim (DE); Juergen Langewald, Mannheim (DE)

(73) Assignee: BASF SE, Ludwigshafen (DE)

( * ) Notice: Subject to any disclaimer, the term of this patent is extended or adjusted under 35 U.S.C. 154(b) by 152 days.

(21) Appl. No.: 13/700,182

(22) PCT Filed: May 27, 2011

(86) PCT No.: PCT/EP2011/058704  
§ 371 (c)(1),  
(2), (4) Date: Nov. 27, 2012

(87) PCT Pub. No.: WO2011/147952  
PCT Pub. Date: Dec. 1, 2011

(65) Prior Publication Data  
US 2013/0125267 A1    May 16, 2013

Related U.S. Application Data

(60) Provisional application No. 61/349,228, filed on May 28, 2010.

(30) Foreign Application Priority Data

May 28, 2010 (EP) .................. 10164305

(51) Int. Cl.  
*A01N 53/00* (2006.01)  
*A01N 43/90* (2006.01)  
*A01N 43/40* (2006.01)

(52) U.S. Cl.  
CPC ............... *A01N 53/00* (2013.01); *A01N 43/40* (2013.01); *A01N 43/90* (2013.01)

(58) Field of Classification Search  
CPC ....... A01N 43/90; A01N 53/00; A01N 43/40; A01N 2300/00  
See application file for complete search history.

(56) References Cited

U.S. PATENT DOCUMENTS

| 7,491,738 | B2 | 2/2009 | Goto et al. |
| 8,263,778 | B2 | 9/2012 | Goto et al. |
| 2010/0113525 | A1 | 5/2010 | Horikoshi et al. |
| 2010/0281584 | A1 | 11/2010 | Horikoshi et al. |

FOREIGN PATENT DOCUMENTS

| EP | 2 107 060 | 10/2009 | | |
| EP | 2 119 361 | 11/2009 | | |
| EP | 2223599 | * 1/2010 | ............. | A01N 43/90 |
| EP | 2 223 599 | 9/2010 | | |
| JP | WO2006/129714 | * 7/2006 | ............. | A01N 43/90 |
| JP | EP2223599 | * 1/2009 | ............. | A01N 43/90 |
| WO | WO 2006/129714 | 12/2006 | | |
| WO | WO 2008/108491 | 9/2008 | | |
| WO | WO 2009/022702 | 2/2009 | | |
| WO | WO 2009/081851 | 7/2009 | | |
| WO | WO 2011/147953 | 12/2011 | | |

OTHER PUBLICATIONS

Joan Lasota & Richard Dybas, Avermectins, a Novel Class of Compounds: Implications for use in Arthropod Pest Control, 36 Annu. Rev. Entomol. 91 (1991).*  
Certified Translation of WO2006/129714.*  
Office Action dated May 12, 2014 from U.S. Appl. No. 13/700,180.  
Bartlett, Dave W., "Review, The strobilurin fungicides", Pest Manafement Science, online:2002, p. 649-662, vol. 58.  
International Search Report dated Jul. 7, 2011, prepared in International Application No. PCT/EP2011/058704, filed May 27, 2011.  
International Preliminary Report on Patentability dated Dec. 4, 2012, prepared in International Application No. PCT/EP2011/058704, filed May 27, 2011.

* cited by examiner

*Primary Examiner* — Sean Basquill  
(74) *Attorney, Agent, or Firm* — Brinks Gilson & Lione

(57) ABSTRACT

The present invention, comprising: [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cydopropanecarboxylate (compound II) and a pesticidal compound II; in synergistic effective amounts.

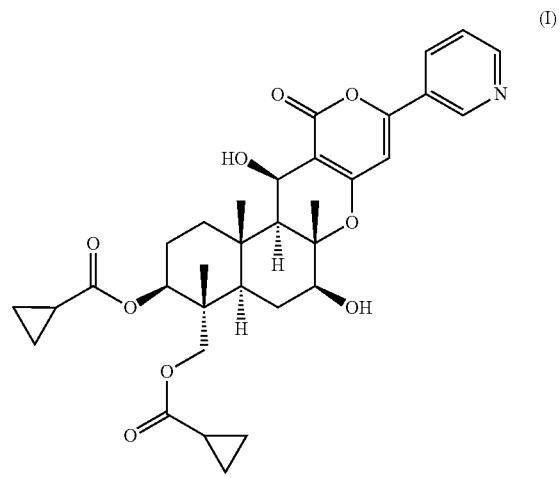

(I)

16 Claims, No Drawings

PESTICIDAL MIXTURES

This application is a National Stage application of International Application No. PCT/EP2011/058704, filed May 27, 2011, which claims the benefit of U.S. Provisional Application No. 61/349,228 filed May 28, 2010, the entire contents of which are hereby incorporated herein by reference. This application also claims priority under 35 U.S.C. §119 to European Patent Application No. 10164305.4, filed May 28, 2010, the entire contents of which is hereby incorporated herein by reference.

The present invention relates to synergistic mixtures comprising, as active components, 1) the pesticidal compound of formula I

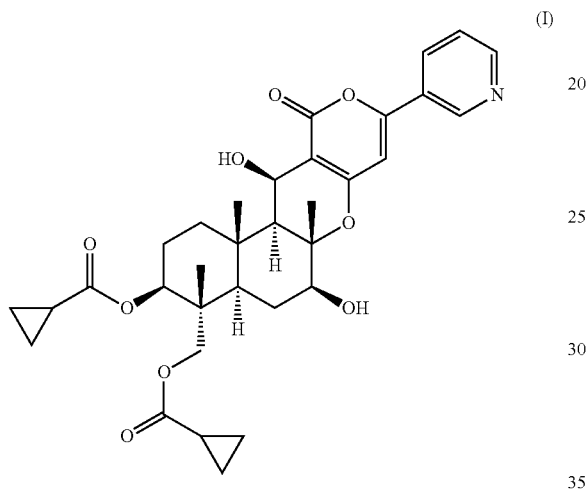

and 2) one or more, e.g. 1, 2 or 3, in particular one, pesticidal compound II selected from the compounds of following groups M.1. to M.28 as defined herein:

M.1. Organo(thio)phosphate compounds selected from the group consisting of acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. Carbamate compounds selected from the group consisting of aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate;

M.3. Pyrethroid compounds selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, ethofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin(pyrethrum), resmethrin, silafluofen, tefluthrin, tetramethrin, tralomethrin and transfluthrin;

M.4. Juvenile hormone mimics selected from the group consisting of hydroprene, kinoprene, methoprene, fenoxycarb and pyriproxyfen;

M.5. Nicotinic receptor agonists/antagonists compounds consisting of acetamiprid, bensultap, cartap hydrochloride, clothianidin, dinotefuran, imidacloprid, thiamethoxam, nitenpyram, nicotine, spinosad (allosteric agonist), spinetoram(allosteric agonist), thiacloprid, thiocyclam, thiosultap-sodium and AKD1022, i.e. 1-[(2-chloro-1,3-thiazol-5-yl)methyl]-3,5-dimethyl-N-nitro-1,3,5-triazinan-2-imine;

M.6. GABA gated chloride channel antagonist compounds selected from the group consisting of chlordane, endosulfan, gamma-HCH (lindane); ethiprole, fipronil, pyrafluprole and pyriprole;

M.7. Chloride channel activators selected from the group consisting of abamectin, emamectin benzoate, milbemectin and lepimectin;

M.8. METI I compounds selected from the group consisting of fenazaquin, fenpyroximate, pyrimidifen, pyridaben, tebufenpyrad, tolfenpyrad, flufenerim and rotenone;

M.9. METI II and III compounds selected from the group consisting of acequinocyl, fluacyprim and hydramethylnon;

M.10. Uncouplers of oxidative phosphorylation selected from the group consisting of chlorfenapyr and DNOC, i.e. 4,6-dinitro-2-methylphenol;

M.11. Inhibitors of oxidative phosphorylation selected from the group consisting of azocyclotin, cyhexatin, diafenthiuron, fenbutatin oxide, propargite and tetradifon;

M.12. Moulting disruptors selected from the group consisting of cyromazine, chromafenozide, halofenozide, methoxyfenozide and tebufenozide;

M.13. Synergists selected from the group consisting of piperonyl butoxide and tribufos;

M.14. Sodium channel blocker compounds selected from the group consisting of indoxacarb and metaflumizone;

M.15. Fumigants selected from the group consisting of methyl bromide, chloropicrin and sulfuryl fluoride;

M.16. Selective feeding blockers selected from the group consisting of cryolite, pymetrozine and flonicamid;

M.17. Mite growth inhibitors selected from the group consisting of clofentezine, hexythiazox and etoxazole;

M.18. Chitin synthesis inhibitors selected from the group consisting of buprofezin, bistrifluron, chlorfluazuron, diflubenzuron, flucycloxuron, flufenoxuron, hexaflumuron, lufenuron, novaluron, noviflumuron, teflubenzuron and triflumuron;

M.19. Lipid biosynthesis inhibitors selected from the group consisting of spirodiclofen, spiromesifen and spirotetramat; and M.20. the octapaminergic agonsit amitraz; and M.21. Ryanodine receptor modulators selected from the group consisting of flubendiamide and the phtalamid compound (R)-, (S)-3-chlor-N1-{2-methyl-4-[1,2,2,2-tetrafluor-1-(trifluormethyl)ethyl]phenyl}-N2-(1-methyl-2-methylsulfonylethyl)phthalamid (M21.1);

M.22. Isoxazoline compounds selected from the group consisting of 4-[5-(3,5-dichloro-phenyl)-5-trifluoromethyl-4,5-dihydro-isoxazol-3-yl]-2-methyl-N-pyridin-2-ylmethyl-benzamide (M22.1), 4-[5-(3,5-dichlorophenyl)-5-trifluoromethyl-4,5-dihydro-isoxazol-3-yl]-2-methyl-N-(2,2,2-trifluoro-ethyl)-benzamide (M22.2), 4-[5-(3,5-dichloro-phenyl)-5-trifluoromethyl-4,5-dihydro-isoxazol-3-yl]-2-methyl-N-[(2,2,2-trifluoroethylcarbamoyl)-methyl]-benzamide (M22.3), 4-[5-(3,5-dichlorophenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) 4-[5-(3,5-dichlorophenyl)-5-trifluoromethyl-4,5-dihydro-isoxazol-3-yl]-N-[(methoxyimino)methyl]-2-methylbenzamide (M22.5) 4-[5-(3-chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6); 4-[5-(3-chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds selected from the group consisting of chloranthraniliprole, cyantraniliprole, 5-bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-bromo-2-(3-chloro-pyridin-2-yl)-2H-pyrazole-3-carboxylic acid [2,4-dichloro-6-(1-cyclopropyl-ethylcarbamoyl)-phenyl]amide (M23.5), 5-bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds selected from the group consisting of 2-(2,2,3,3,4,4,5,5-octafluoropentyl)-2-(3,3,3-trifluoro-propyl)malononitrile ($CF_2H$—$CF_2$—$CF_2$—$CF_2$—$CH_2$—$C(CN)_2$—$CH_2$—$CH_2$—$CF_3$) (M24.1) and 2-(2,2,3,3,4,4,5,5-octafluoropentyl)-2-(3,3,4,4,4-pentafluorobutyl)-malonodinitrile ($CF_2H$—$CF_2$—$CF_2$—$CF_2$—$CH_2$—$C(CN)_2$—$CH_2$—$CH_2$—$CF_2$—$CF_3$) (M24.2);

M.25. Microbial disruptors selected from the group consisting of *Bacillus thuringiensis* subsp. *Israelensi*, *Bacillus sphaericus*, *Bacillus thuringiensis* subsp. *Aizawai*, *Bacillus thuringiensis* subsp. *Kurstaki* and *Bacillus thuringiensis* subsp. *Tenebrionis*;

M.26. Aminofuranone compounds selected from the group consisting of 4-{[(6-Bromopyrid-3-yl)methyl] (2-fluoroethyl)amino}furan-2(5H)-on (M26.1), 4-{[(6-Fluoropyrid-3-yl)methyl](2,2-difluoroethyl) amino}furan-2(5H)-on (M26.2), 4-{[(2-Chloro 1, 3-thiazolo-5-yl)methyl](2-fluoroethyl)amino}furan-2(5H)-on (M26.3), 4-{[(6-Chloropyrid-3-yl)methyl] (2-fluoroethyl)amino}furan-2(5H)-on (M26.4), 4-{[(6-Chloropyrid-3-yl)methyl](2,2-difluoroethyl) amino}furan-2(5H)-on (M26.5), 4-{[(6-Chloro-5-fluoropyrid-3-yl)methy](methyl)amino}furan-2 (5H)-on (M26.6), 4-{[(5,6-Dichloropyrid-3-yl) methyl](2-fluoroethyl)amino}furan-2(5H)-on (M26.7), 4-{[(6-Chloro-5-fluoropyrid-3-yl)methyl] (cyclopropyl)amino}furan-2(5H)-on (M26.8), 4-{[(6-Chloropyrid-3-yl)methyl](cyclopropyl) amino}furan-2(5H)-on (M26.9) and 4-{[(6-Chloropyrid-3-yl)methyl](methyl)amino}furan-2(5H)-on (M26.10);

M.27. the insceiticides selected from the group consisting of aluminum phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N-R'-2,2-dihalo-1-R"cyclo-propanecarboxamide-2-(2,6-dichloro-α,α,α-trifluoro-p-tolyl)hydrazone or N-R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 8-(2-cyclopropylmethoxy-4-trifluoromethyl-phenoxy)-3-(6-trifluoromethyl-pyridazin-3-yl)-3-aza-bicyclo[3.2.1]octane (M27.3); and M28: the bacillus species selected from the group consisting of species *Bacillus firmus* CNCM 1-1582 and *Bacillus cereus* strain CNCM 1-1562; wherein the ratio by weight of compound I and compound II is from 1:500 to 500:1, frequently from 1:100 to 100:1, in particular from 1:50 to 50:1 and especially from 1:25 to 25:1.

These above-referred mixtures are hereinbelow also referred as "inventive mixtures". The inventive mixtures show synergistic action against animal pests, e.g. against invertebrate pests such as insects, acarids or nematodes, in particular against arthropod pests such as insects or acarids and especially against insects, i.e. the activity of the inventive mixtures against these pests is higher that it would have been expected from the known activity of the individual compounds against these pests.

Therefore, the present invention also relates to the use of the mixtures as described herein for controlling animal pests, in particular invertebrate pests such as insects, acarids or nematodes, especially arthropod pests such as insects and acarids.

Moreover, the invention relates to a method for controlling pests, this refers to includes phytopathogenic animal pests (in particular invertebrate pests such as insects, acarids or nematodes, especially arthropod pests such as insects and acarids), using the inventive mixtures and to the use of compound I and compound II for preparing such mixtures, and also to compositions comprising such mixtures.

In one embodiment, the present invention provides methods for the control of phytopathogenic animal pests (in particular invertebrate pests such as insects, acarids or nematodes, especially arthropod pests such as insects and acarids) comprising contacting the animal pest (the insect, acarid or nematode) or their food supply, habitat, breeding grounds or their locus with a pesticidally effective amount of the inventive mixtures.

Moreover, in another embodiment the present invention also relates to a method of protecting plants from attack or infestation by phytopathogenic animal pests (in particular invertebrate pests such as insects, acarids or nematodes, especially arthropod pests such as insects and acarids) comprising contacting the plant, or the soil or water in which the plant is growing, or the plant propagation material with a pesticidally effective amount of the inventive mixture.

Preferably, the present invention also comprises a method for protection of plant propagation material from animal pests (in particular invertebrate pests such as insects, arachnids or nematodes, especially arthropod pests such as insects and acarids) comprising contacting the plant propagation materials with an inventive mixture in pesticidally effective amounts. The invention also comprises plant propagation material treated with an inventive mixture.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. In a particular preferred embodiment, the term propagation material denotes seeds.

The present invention further relates to plant-protecting active ingredient mixtures having synergistically enhanced action of improving the health of plants and to a method for improving the health of plants and/or increasing the yield, wherein the plant, the locus where the plant is growing or is expected to grow or plant propagation material from which the plant grows is treated with an effective amount of an inventive mixture.

The compounds I and II as well as their pesticidal action and methods for producing them are generally known.

For instance, the commercially available compounds of group II may be found in The Pesticide Manual, 14th Edition, British Crop Protection Council (2006) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822, 779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540.-The alkynylether compound M271 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. Malononitrile compounds as those (M24.1) and (M24.2) have been described in WO 02/089579, WO 02/090320, WO 02/090321, WO 04/006677, WO 05/068423, WO 05/068432 and WO 05/063694. The compound of formula I, which has the IPAC name [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl] methyl cyclopropanecarboxylate as well as its pesticidal action has been described in WO2006/129714 and WO2009/081851, insecticidal mixtures thereof in WO2008/108491and methods for producing the compound are for example disclosed in WO2009/022702.

*Bacillus firmus* CNCM 1-1582 spore and/or *B. cereus* strain CNCM 1-1562 spore as disclosed in U.S. Pat. No. 6,406,690, which is incorporated herein by reference in its entirety.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of animal pests, which have developed natural or adapted resistance against the active compound in question. Therefore there is a need for pest control agents that help prevent or overcome resistance.

Another problem underlying the present invention is the desire for compositions that improve plants, a process which is commonly and hereinafter referred to as “plant health”.

The term “plant health” comprises various sorts of improvements of plants that are not connected to the control of pests. For example, advantageous properties that may be mentioned are improved crop characteristics including: emergence, crop yields, protein content, oil content, starch content, more developed root system (improved root growth), improved stress tolerance (e.g. against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination; or any other advantages familiar to a person skilled in the art.

If used in connection with the treatment of plant propagation material (preferably seeds) the term "plant health" is equivalent with " seed vitality". Seed vitality manifests itself in a variety of factors. Examples of factors which are manifestations of the plant's vitality are:
(a) overall visual appearance;
(b) root growth and/or root development;
(c) size of the leaf area;
(d) intensity of the leaves' green coloration;
(e) number of dead leaves in the vicinity of the ground;
(f) plant height;
(g) plant weight;
(h) growth rate;
(i) plant stand density;
(j) germination behavior;
(k) emergence behavior;
(l) shoot number;
(m) shoot type (quality and productivity)
(n) toughness of the plant, for example resistance to biotic or abiotic stress;
(o) presence of necroses;
(p) senescence behavior.

Preferably, the term " Seed vitality" denotes plant stand density, storability of seeds and/or germination behavior.

A further object of various efforts in crop protection is to increase the yield of plants. "Yield" is to be understood as any plant product of economic value that is produced by the plant such as grains, fruits in the proper sense, vegetables, nuts, grains, seeds, wood (e.g. in the case of silviculture plants) or even flowers (e.g. in the case of gardening plants, ornamentals). The plant products may in addition be further utilized and/or processed after harvesting.

According to the present invention, "increased yield" of a plant, in particular of an agricultural, silvicultural and/or horticultural plant, preferably agricultural plant means that the yield of a product of the respective plant is increased by a measurable amount over the yield of the same product of the plant produced under the same conditions, but without the application of the mixture according to the invention.

Increased yield can be characterized, among others, by following improved properties of the plant:
increased plant weight
increased plant height
increased biomass such as higher overall fresh weight (FW)
higher grain yield
more tillers
larger leaves
increased shoot growth
increased protein content
increased oil content
increased starch content
increased pigment content.

According to the present invention, the yield is increased by at least 2%, preferable by at least 4%, more preferred by at least 8%, even more preferred by at least 16%).

EP 2119361 and EP 2223599 disclose several pesticidal mixtures which may, inter alia, comprise the compound of formula I.

However, the outstanding synergistic pestidical and/or plant health action of the specific inventive mixtures as well as the as defined at the outset are not disclosed therein, also not, that such combinations might have and especially its suitability for seed treatment purposes.

It was therefore an object of the present invention to provide pesticidal mixtures which solve the problems of reducing the dosage rate and/or enhancing the spectrum of activity and/or combining knock-down activity with prolonged control and/or to resistance management and/or promoting the health of plants.

It was also an object of the present invention to provide methods of increasing the health of plants.

We have found that this object is in part or in whole achieved by the mixtures comprising the active compounds defined in the outset and hereinafter.

Herein, we have found a method for increasing the health of plants, wherein the plant, the locus where the plant is growing or is expected to grow or plant propagation material from which the plant grows is treated with an effective amount of the compound of formula I, wherein preferably the plant propagation material from which the plant grows is treated with an effective amount of the compound of formula I. Such latter treatment of plant propagation material leads to increase in seed vitality.

We have also found method for increasing the health of plants, wherein the plant, the locus where the plant is growing or is expected to grow or plant propagation material from which the plant grows is treated with an effective amount of a compound of formula I and one ore more compounds II, wherein preferably the plant propagation material from which the plant grows is treated with an effective amount of the compound of formula I and one or more compounds II. Such latter treatment of plant propagation material leads to increase in seed vitality.

It has been found that the mixtures as defined in the outset show markedly enhanced action against animal pests (such as insects, arachnids or nematodes) compared to the control rates that are possible with the individual compounds and/or is suitable for improving the health of plants when applied to plants, parts of plants, plant propagation materials (preferably seeds), or at their locus of growth.

It has been found that the action of the inventive mixtures goes far beyond the pesticidal action (action against insects, arachnids and nematodes) and/or plant health improving action of the active compounds present in the mixture alone (synergism).

In particular, it has been found that the action of the inventive mixtures goes far beyond the pesticidal (action against insects, arachnids and nematodes and/or plant health improving action of the active compounds present in the mixture alone (synergism) if applied as a seed treatment.

Thus, these mixtures are also suitable for improving the health of plants when applied to plants, parts of plants, seeds, or at their locus of growth, preferably to plants and plant propagation material, more preferably to seeds.

Moreover, we have found that simultaneous, that is joint or separate, application of the compound I and the compound II or successive application of the compound I and the compound II allows enhanced control of animal pests, compared to the control rates that are possible with the individual compounds (synergistic pesticidal mixtures).

Moreover, we have found that simultaneous, that is joint or separate, application of the compound I and compound II or successive application of the compound I and compound II provides enhanced plant health effects compared to the plant health effects that are possible with the individual compounds (synergistic mixtures wherein the synergism is plant health synergism).

Hereinbelow, the compound of formula I is named "compound I".

In general, the ratios by weight for the respective mixtures comprising the insecticidal compound I and compound II are from 1:500 to 500:1, preferably from 1:100 to 100:1, in particular from 1:50 to 50:1 and more preferably from 1:25 to 25:1.

Preference is also given to mixtures comprising the compound I and as compound II a pesticide selected from group M.3, and particularly selected from alpha-cypermethrin, bifenthrin, cypermethrin, deltamethrin, flucythrinate, lambda-cyhalothrin, tefluthrin and permethrin, where the compound I and the compound of the group M.3 is present in particular in synergistically effective amounts, preferably in a ratio by weight of compound I to compound M.3 from 1:500 to 500:1, preferably from 1:100 to 100:1, in particular from 1:50 to 50:1 and more preferably from 1:25 to 25:1.

Particular preference is given to mixtures comprising or consisting of the compound I and bifenthrin. In this mixture, the compound I and bifenthrin are preferably present in synergistically effective amounts, preferably in a ratio by weight of compound I to bifenthrin from 1:500 to 500:1, preferably from 1:100 to 100:1, in particular from 1:50 to 50:1 and more preferably from 1:25 to 25:1.

Particular preference is also given to mixtures comprising or consisting of the compound I and alpha-cypermethrin. In this mixture, the compound I and apha-cypermethrin are preferably present in synergistically effective amounts, preferably in a ratio by weight of compound I to alpha-cypermethrin from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.5, which is preferably selected from the group consisting of bensultap, cartap hydrochloride, nitenpyram, nicotine, spinosad, spinetoram, thiacloprid, thiocyclam, thiosultap-sodium and AKD1022, particularly selected from the group consisting of acetamiprid, clothianidin, dinotefuran, imidacloprid, thiamethoxam, nitenpyram, spinosad, spinetoram and thiacloprid and especially selected from the group consisting of nitenpyram, spinosad, spinetoram and thiacloprid. In these mixtures, the compound I and the compound selected form the group M.5 are preferably present in in synergistically effective amounts, preferably in a ratio by weight of compound I to compound M.5 from 1:500 to 500:1, preferably from 1:100 to 100:1, in particular from 1:50 to 50:1 and more preferably from 1:25 to 25:1.

Particular preference is given to mixtures comprising or consisting of the compound I and spinosad. In this mixture, the compound I and spinosad are preferably present in synergistically effective amounts, preferably in a ratio by weight of compound I to spinosad from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.6, and particularly selected from the group consisting of ethiprole and fipronil. In these mixtures, the compound I and the compound selected form the group M.6 are preferably present in in synergistically effective amounts, preferably in a ratio by weight of compound I to compound M.6 from 1:500 to 500:1, preferably from 1:100 to 100:1, in particular from 1:50 to 50:1 and more preferably from 1:25 to 25:1.

Particular preference is given to mixtures comprising or consisting of the compound I and ethiprole. In this mixture, the compound I and ethiprole are preferably present in synergistically effective amounts, preferably in a ratio by weight of compound I to ethiprole from 1:500 to 500:1, preferably from 1:100 to 100:1, in particular from 1:50 to 50:1 and more preferably from 1:25 to 25:1.

Particular preference is also given to mixtures comprising or consisting of the compound I and fipronil. In this mixture, the compound I and fipronil are preferably present in synergistically effective amounts, preferably in a ratio by weight of compound I to fipronil from 1:500 to 500:1, preferably from 1:100 to 100:1, in particular from 1:50 to 50:1 and more preferably from 1:25 to 25:1.

Preference is also given to mixtures comprising or consisting of the compound I and pymetrozine. In this mixture, the compound I and pymetrozine are preferably present in synergistically effective amounts, preferably in a ratio by weight of compound I to pymetrozine from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.7, and particularly selected from the group consisting of abamectin, emamectin benzoate, milbemectin and lepimectin. In these mixtures, the compound I and the compound selected from the group M.7 are preferably present in in synergistically effective amounts, preferably in a ratio by weight of compound I to compound M.7 from 1:500 to 500:1, preferably from 1:100 to 100:1, in particular from 1:50 to 50:1 and more preferably from 1:25 to 25:1.

Particular preference is also given to mixtures comprising or consisting of the compound I and abamectin. In this mixture, the compound I and abamectin are preferably present in synergistically effective amounts, preferably in a ratio by weight of compound I to abamectin from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.14, and particularly metaflumizone. In these mixtures, the compound I and the compound selected from the group M.14 are preferably present in synergistically effective amounts, preferably in a ratio by weight of compound I to compound M.14 from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.23, and particularly selected from chloranthraniliprole and cyantraniliprole. In these mixtures, the compound I and the compound selected from the group M.23 are preferably present in synergistically effective amounts, preferably in a ratio by weight of compound I to compound M.23 from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.26, and particularly 4-{[(6-chloropyrid-3-yl)methyl](2,2-difluoroethyl)amino}furan-2(5H)-on (Compound M.26.5). In these mixtures, the compound I and the compound selected from the group M.26. are preferably present in synergistically effective amounts, preferably in a ratio by weight of compound I to compound M.26 from 1:500 to 500:1, preferably from 1:100 to 100:1, in particular from 1:50 to 50:1 and more preferably from 1:25 to 25:1.

Preference is also given to mixtures comprising or consisting of the compound I and sulfoxaflor. In this mixture, the compound I and sulfoxaflor are preferably present in synergistically effective amounts, preferably in a ratio by weight of compound I to sulfoxaflor from 1:500 to 500:1, preferably from 1:100 to 100:1, in particular from 1:50 to 50:1 and more preferably from 1:25 to 25:1.

Preference is also given to mixtures comprising compound I and as compound II a pesticide selected from group M.28, and particularly selected from *Bacillus firmus* CNCM 1-1582 in synergistically effective amounts.

A particular embodiment of the invention relates to mixtures comprising or consisting of the compound I and pesticidal compound II, where the compound II is selected from the group consisting of abamectin, bifenthrin, alpha-cypermethrin, metaflumizone, pymetrozine, chloranthraniliprole, cyanantraniliprole, sulfloxaflor, spinosad and 4-{[(6-chloropyrid-3-yl)methyl](2,2-difluoroethyl)amino}furan-2(5H)-on. In these mixtures, the compound I and the compound II are preferably present in synergistically effective amounts, preferably in a ratio by weight of compound I to compound II from 1:500 to 500:1, preferably from 1:100 to 100:1, in particular from 1:50 to 50:1 and more preferably from 1:25 to 25:1.

Another particular embodiment of the invention relates to mixtures comprising or consisting of the compound I and pesticidal compound II, where the compound II is selected from the group consisting of abamectin, bifenthrin, and 4-{[(6-chloropyrid-3-yl)methyl](2,2-difluoroethyl)amino}furan-2(5H)-on. In these mixtures, the compound I and the compound II are preferably present in synergistically effective amounts, preferably in a ratio by weight of compound I to compound II from 1:500 to 500:1, preferably from 1:100 to 100:1, in particular from 1:50 to 50:1 and more preferably from 1:25 to 25:1.

As mentioned at the outset, the inventive mixtures are in a preferred embodiment used as a seed treatment. For the purpose of seed treatment, the following mixtures are preferred:

Mixtures comprising compound I and as compound II alpha-cypermethrin or tefluthrin, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Mixtures comprising compound I and as compound II clothianidin, imidacloprid, thiamethoxam, acetamiprid, dinotefuran, spinosad or spinetoram, in particular spinetoram or spinosad, preferably in synergistically effective amounts, preferably in a ratio by weight of compound 1:11 from 1:500 to 500:1, preferably from 1:100 to 100:1, in particular from 1:50 to 50:1 and more preferably from 1:25 to 25:1.

Mixtures comprising compound I and as compound II fipronil, preferably in synergistically effective amounts, preferably in a ratio by weight of compound I to fipronil from 1:500 to 500:1, preferably from 1:100 to 100:1, in particular from 1:50 to 50:1 and more preferably from 1:25 to 25:1.

Mixtures comprising compound I and as compound II abamectin, preferably in synergistically effective amounts, preferably in a ratio by weight of compound 1:11 from 1:500 to 500:1, preferably from 1:100 to 100:1, in particular from 1:50 to 50:1 and more preferably from 1:25 to 25:1.

Mixtures comprising compound I and as compound II chloranthraniliprole, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Mixtures comprising compound I and as compound II *Bacillus firmus* CNCM 1-1582 in synergistically effective amounts.

For the purpose of seed treatment, the following mixtures are most preferred:

Mixtures comprising compound I and as compound II chloranthraniliprole, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Mixtures comprising compound I and as compound II abamectin, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Mixtures comprising compound I and as compound II spinosad, preferably in synergistically effective amounts, preferably in a ratio by weight of compound 1:11 from 1:500 to 500:1, preferably from 1:100 to 100:1, in particular from 1:50 to 50:1 and more preferably from 1:25 to 25:1.

Mixtures comprising compound I and as compound II spinetoram, preferably in synergistically effective amounts, preferably in a ratio by weight of compound 1:11 from 1:500 to 500:1, preferably from 1:100 to 100:1, in particular from 1:50 to 50:1 and more preferably from 1:25 to 25:1.

Mixtures comprising compound I and as compound II *Bacillus firmus* CNCM 1-1582 in synergistically effective amounts.

For the purpose of seed treatment, the following mixtures are most preferred:

Mixtures comprising compound I and as compound II chloranthraniliprole, preferably in synergistically effective amounts, preferably in a ratio by weight of compound 1:11 from 1:500 to 500:1, preferably from 1:100 to 100:1, in particular from 1:50 to 50:1 and more preferably from 1:25 to 25:1.

Mixtures comprising compound I and as compound II abamectin, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Mixtures comprising compound I and as compound II spinosad, preferably in synergistically effective amounts, preferably in a ratio by weight of compound I:11 from 1:500 to 500:1, preferably from 1:100 to 100:1, in particular from 1:50 to 50:1 and more preferably from 1:25 to 25:1.

Each of the above-mentioned inventive mixtures can further comprise one or more insecticides, fungicides, herbicides.

For use according to the present invention, the mixtures according to the invention can be converted into the customary formulations, for example solutions, emulsions, suspensions, dusts, powders, pastes and granules. The use form depends on the particular intended purpose; in each case, it should ensure a fine and even distribution of the mixtures according to the present invention. The formulations are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical formulations may also comprise auxiliaries which are customary in agrochemical formulations. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers. Suitable surfactants (adjuvants, wetters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany),and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers therof.

Examples for thickeners (i. e. compounds that impart a modified flowability to formulations, i. e. high viscosity under static conditions and low viscosity during agitation) are polysaccharides and organic and anorganic clays such as Xanthan gum (Keizan®, CP Kelco, U.S.A.), Rhodopol® 23 (Rhodia, France), Veegum® (R.T. Vanderbilt, U.S.A.) or Attaclay® (Engelhard Corp., N.J., USA).

Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds the resepective active compounds present in the inventive mixtures and, if appropriate, further active substances, with at least one solid carrier.

Granules, e. g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Examples for formulation types are:
1. Composition Types for Dilution with Water
  i) Water-Soluble Concentrates (SL, LS)
  10 parts by weight of compounds of the inventive mixtures are dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.
  ii) Dispersible Concentrates (DC)
  20 parts by weight of compounds of the inventive mixtures are dissolved in 70 parts by weight of cyclohexanone with addition of 10 parts by weight of a dispersant, e. g. polyvinylpyrrolidone. Dilution with water gives a dispersion. The active substance content is 20% by weight.
  iii) Emulsifiable Concentrates (EC)
  15 parts by weight of compounds of the inventive mixtures are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
  iv) Emulsions (EW, EO, ES)
  25 parts by weight of compounds of the inventive mixtures are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of compounds of the inventive mixtures are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of compounds of the inventive mixtures are ground finely with addition of 50 parts by weight of dispersants and wetting agents and prepared as water-dispersible or water-soluble granules by means of technical appliances (e. g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of compounds of the inventive mixtures are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of compounds of the inventive mixtures are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be applied Undiluted ix) Dustable Powders (DP, DS)

5 parts by weight of compounds of the inventive mixtures are ground finely and mixed intimately with 95 parts by weight of finely divided kaolin. This gives a dustable composition having an active substance content of 5% by weight.

x) Granules (GR, FG, GG, MG)

0.5 parts by weight of compounds of the inventive mixtures is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of compounds of the inventive mixtures are dissolved in 90 parts by weight of an organic solvent, e. g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The compounds of the inventive mixtures are employed in a purity of from 90% to 100%, preferably from 95% to 100% (according to NMR spectrum).

The compounds of the inventive mixtures can be used as such or in the form of their compositions, e. g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive mixtures.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive mixtures.

The compounds of the inventive mixtures may also be used successfully in the ultralow-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive mixtures in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

The compounds contained in the mixtures as defined above can be applied simultaneously, that is jointly or separately, or in succession, the sequence, in the case of separate application, generally not having any effect on the result of the control measures.

According to this invention, the compound I and compound II is to be understood to denote, that at least the compound I and compound II occur simultaneously at the site of action (i.e. the animal pests such as insects, arachnids or nematodes to be controlled or their habitats such as infected plants, plant propagation materials, particularly seeds, surfaces, materials or the soil as well as plants, plant propagation materials, particularly seeds, soil, surfaces, materials or rooms to be protected from fungal or animal attack) in a effective amount.

This can be obtained by applying the compound I and compound II simultaneously, either jointly (e. g. as tank-mix) or sperately, or in succession, wherein the time interval between the individual applications is selected to ensure that the active substance applied first still occurs at the site of action in a sufficient amount at the time of application of the further active substance(s). The order of application is not essential for working of the present invention.

In the mixtures of the present invention, the weight ratio of the compounds generally depends from the properties of the compounds of the inventive mixtures.

The compounds of the inventive mixtures can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E. g., kits may include the compound I and compound II and/or an adjuvant component and/or a further pesticidal compound (e.g. insecticide or herbicide) and/or a growth regulator component). One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i. e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual compounds of the inventive mixtures formulated as composition (or formulation) such as parts of a kit or parts of the inventive mixture may be mixed by the user himself in a spray tank and further auxiliaries may be added, if appropriate (tank mix).

In a further embodiment, either individual compounds of the inventive mixtures formulated as composition or partially premixed components, e. g. components comprising the compound I and compound II may be mixed by the user in a spray tank and further auxiliaries and additives may be added, if appropriate (tank mix).

In a further embodiment, either individual components of the composition according to the invention or partially premixed components, e. g. components comprising the compound I and compound I, can be applied jointly (e. .g. after tankmix) or consecutively.

As said above, the present invention comprises a method for controlling animal pests, in particular arthropod pests, especially arthropod pests from the group of insects, wherein the pest, their habitat, breeding grounds, their locus or the plants to be protected against pest attack, the soil or plant propagation material (preferably seed) are treated with an pesticidally effective amount of a mixture.

The method of the invention does not include methods for the therapeutical treatment of the human or animal body.

The inventive mixtures exhibit also outstanding action against animal pests from the following orders:

insects from the order of the lepidopterans (*Lepidoptera*), for example *Agrotis ypsllon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini; Diaphania nitdalis, Diatraea grandiosella, Earias insulana, Elasmopalpus lignosellus, Eupoecllia ambiguella, Evetria bouliana, Feltia subterranea, Galleria mellonella, Grapholitha funebrana, Grapholitha molesta, Heliothis armigera, Heliothis virescens, Heliothis zea, Hellula undalls, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis Oleriana, Spodoptera frugiperda, Spodoptera littoralis, Spodoptera litura, Thaumatopoea pityocampa, Tortrix viridana, Trichoplusia ni* and *Zeiraphera canadensis*, beetles (*Coleoptera*), for example *Agrilus sinuatus, Agriotes lineatus, Agriotes obscurus, Amphimallus solstitials, Anisandrus dispar, Anthonomus gandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimillis, Ceuthorrhynchus napi, Chaetocnema tibialis, Conoderus vespertinus, Criocenis asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneippennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophllus granaria*, flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops Chrysops sllacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprin, Lucilia cuprina, Lucilia sericata, Lycoria pectoralis, Mansonia titillanus, Mayetiola destructor, Musca domestica, Muscina stabulans, Oestrus ovis, Opomyza forum, Oscinella frit, Pegomya hysocyami, Phorbia antiqua, Phorbia brassicae,*

*Phorbia coarctate, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus Tipula oleracea,* and *Tipula paludosa* thrips (*Thysanoptera*), e.g. *Dichromothrips corbetti, Dichromothrips* ssp, *Frankliniella fusca, Frankliniella occidentalis, Frankliniella tritici, Sartothrips citri, Thrips oryzae, Thrips palmi* and *Thrips tabaci;* termites (*Isoptera*), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (*Blattaria-Blattodea*), e.g. *Blattella germanica, Blattella asahinae, Periplaneta americana, Periplaneta japonica, Periplaneta brunnea, Periplaneta fulliginosa, Periplaneta australasiae,* and *Blatta orientalis,* true bugs (*Hemiptera*), e.g. *Acrosternum Mare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perdllor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum malis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus.* ants, bees, wasps, sawflies (*Hymenoptera*), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsi:s geminata, Solenopsis in victa, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (*Orthoptera*), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,*

Arachnoidea, such as arachnids (*Acarina*), e.g. of the families Argasidae, Ixodidae and Sarcoptidae, such as *Amblyomma americanum, Amblyomma variegaturn, Ambryomma maculatum, Argas persicus, Boophilus annulatus, Boophilus decoloratus, Boophilus microplus, Dermacentor silvarum, Dermacentorandersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis; Araneida,* e.g. *Latrodectus mactans,* and *Loxosceles reclusa,* fleas (*Siphonaptera*), e.g. *Ctenocephalides felis, Ctenocephalides canis, Xenopsylla cheopis, Pulex irritans, Tunga penetrans,* and *Nosopsyllus fasciatus,* silverfish, firebrat (*Thysanura*), e.g. *Lepisma saccharina* and *Thermobia domestica,* centipedes (*Chilopoda*), e.g. *Scutigera coleoptrata,* millipedes (*Diplopoda*), e.g. *Narceus* spp.,

Earwigs (*Dermaptera*), e.g. *forficula auricularia,* lice (*Phthiraptera*), e.g. *Pediculus humanus capitis, Pediculus humanus corporis, Pthirus pubis, Haematopinus eurystemus, Haematopinus suis, Linognathus vituli, Bovicola bovis, Menopon gallinae, Menacanthus stramineus* and *Solenopotes capillatus,* plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species; seed gall nematodes, *Anguina funesta, Anguina tritici* and other *Anguina* species; stem and foliar nematodes, *Aphe/enchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophllus* and other *Bursaphelenchus* species, ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species, sheath nematodes, *Hemicycliophora* species and *Hemicriconemoides* species; *Hirshmanniella* species; lance nematodes, *Hopolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paraty/enchus* species; Iesion nematodes, *Pratylenchus brachyurus, Pratylenchus coffeae, Praty-*

*lenchus curvitatus, Pratylenchus goodeyi, Pratylencus neglectus, Pratylenchus penetrans, Pratylenchus scnbneri, Pratylenchus vulnus, Pratylenchus zeae* and other *Pratylenchus* species; *Radinaphelenchus cocophllus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor*and other *Paratrichodorus* species, stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudaturn* and other *Xiphinema* species, and other plant parasitic nematode species.

The mixtures according to the invention can be applied to any and all developmental stages of pests, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, plant propagation material (preferably seed), soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the animal pest. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

As said above, the present invention comprises a method for improving the health of plants, wherein the plant, the locus where the plant is growing or is expected to grow or plant propagation material, from which the plant grows, is treated with an plant health effective amount of an inventive mixture.

The term "plant health effective amount" denotes an amount of the inventive mixtures, which is sufficient for achieving plant health effects as defined hereinbelow. More exemplary information about amounts, ways of application and suitable ratios to be used is given below. Anyway, the skilled artisan is well aware of the fact that such an amount can vary in a broad range and is dependent on various factors, e.g. the treated cultivated plant or material and the climatic conditions.

The term "effective amount" comprises the terms "plant health effective amount" and/or "pesticidally effective amount" as the case may be.

When preparing the mixtures, it is preferred to employ the pure active compounds, to which further active compounds, such as insecticides, herbidices, fungicides or else herbicidal or growth-regulating active compounds or fertilizers can be added according to need.

The inventive mixtures are employed by treating the animal pest or the plants, plant propagation materials (preferably seeds), materials or soil to be protected from pesticidal attack with a pesticidally effective amount of the active compounds. The application can be carried out both before and after the infection of the materials, plants or plant propagation materials (preferably seeds) by the pests.

Peferalby, the inventive mixtures are employed by treating the animal pests or the plants or soil to be protected from pesticidal attack via foliar application with a pesticidally effective amount of the active compounds. Also herein, the application can be carried out both before and after the infection of the plants by the pests.

In the method of combating animal pests (insects, acarids or nematodes) depending on the type of compound and the desired effect, the application rates of the mixtures according to the invention are from 0.1 g/ha to 10000 g/ha, preferably 1 g/ha to 5000 g/ha, more preferably from 20 to 1000 g/ha, most preferably from 10 to 750 g/ha, in particular from 20 to 500 g/ha.

In the context of the present invention, the term plant refers to an entire plant, a part of the plant or the propagation material of the plant.

Plants and as well as the propagation material of said plants, which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, mixtures according to the present invention can be applied (as seed treatment, spray treatment, in furrow or by any other means) also to plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (*Coeloptera*), two-winged insects (*Diptera*), and moths (*Lepidoptera*) and to nematodes (*Nematoda*). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphino-thricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The inventive mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non phytophathogenic pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by non-phytophathogenic insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive mixtures, optionally a repellent and at least one binder.

The inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weights %, preferably from 0.01 to 50 weight % and most preferably from 0.01 to 15 weight %.

As mentioned at the outset, in a preferred embodiment of the invention, the inventive mixtures are used for the protection of the seed and the seedlings' roots and shoots, preferably the seeds.

Seed treatment can be made into the seedbox before planting into the field.

For seed treatment purposes, the weight ration in the inventive mixtures generally depends from the properties of the compounds of the inventive mixtures.

Customary formulations, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying the inventive mixture and compositions thereof, respectively, on to plant propagation material, especially seeds, are known in the art, and include but not limited to, seed dressing, seed coating, seed dusting, seed soaking, seed film coating, seed multilayer coating, seed encrusting, seed dripping, and seed pelleting.

In a preferred embodiment, the compounds or the compositions thereof, respectively, are applied on to the plant propagation material by a method such that germination is not induced, e. g. by seed dressing, pelleting, coating and dusting.

In the treatment of plant propagation material (preferably seed), the application rates of the inventive mixture are generally for the formulated product (which usually comprises from 10 to 750 g/l of the active(s)).

The invention also relates to the propagation products of plants, and especially the seed comprising, that is, coated with and/or containing, a mixture as defined above or a composition (customary formulation) comprising the inventive mixture of two or more active ingredients or a mixture of two or more compositions each providing one of the active ingredients. The plant propagation material (preferably seed) comprises the inventive mixtures in an amount of from 0.1 g to 10 kg per 100 kg of plant propagation material (preferably seed), preferably 0.1 g to 1 kg per 100 kg of plant propagation material (preferably seed).

The separate or joint application of the compounds of the inventive mixtures is carried out by spraying or dusting the seeds, the seedlings, the plants or the soils before or after sowing of the plants or before or after emergence of the plants.

In accordance with one variant of soil application, a further subject of the invention is in furrow treatment, which comprises adding a solid or liquid formulation comprising the inventive mixtures to the open furrow, in which seeds have been sown or, alternatively, applying seeds and formulation simultaneously to the open furrow.

The mixtures of the present invention show synergistic action against the animal pests to be controlled. Synergism can be described as an interaction where the combined effect of a mixture of two or more compounds is greater than the sum of the individual effects of each of the compounds. The presence of a synergistic effect, in terms of percent control, between two mixing partners (X and Y) can be calculated using the Colby equation (Colby, S. R., 1967, Calculating Synergistic and Antagonistic Responses in Herbicide Combinations, Weeds, 15, 20-22):

$$E = X + Y - \frac{XY}{100}$$

In Colby's formula X and Y are the % control observed for the individual compounds at a given concentration. E is the expected combined control effect, which would be expected in the absence of synergism, if the compounds were applied together at the same concentrations of solo application. When the control effect observed for the mixture (i.e. the observed combined control effect) is greater than the expected combined control effect (E) as calculated from Colby's formula, then the observed effect is synergistic.

The following tests demonstrate the control efficacy of compounds, mixtures or compositions of this invention on specific pests. The pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions was determined using Colby's equation.

Test 1: Control of Vetch Aphid

For evaluating control of vetch aphid (*Megoura viciae*) through contact or systemic means the test was preformed in a test unit consisting of 24-well-microtiter plates containing broad bean leaf disks.

The individual compounds were formulated as a stock-solution containing 75% v/v water and 25% v/v dimethylsulfoxid (DMSO). The stock-solutions were diluted with water to the desired concentrations of the compounds or mixtures and the dilutions were sprayed onto the leaf disks at 2.5 µl, using a custom built micro atomizer, at two replications. For experimental mixtures in these tests, identical volumes of both mixing partners at the desired concentrations respectively, were mixed together.

After application, the leaf disks were air-dried and 5-8 adult aphids were placed on the leaf disks inside the microtiter plate wells. The aphids were then allowed to suck on the treated leaf disks and incubated at 23±1° C., 50±5% RH for 5 days. Aphid mortality and fecundity was then visually assessed. For the mixture tested the results are listed in table 1.

TABLE 1

Control of Vetch Aphid

| | Concentration [ppm] | Oberved Control average [%] | Calculated Control [%] |
|---|---|---|---|
| Compound I | 0.004 | 25 | — |
| Bifenthrin | 2 | 0 | — |
| Bifenthrin + Compound I | 2 + 0.004 | 100* | 25 |

*synergistic control effect according to Colby's equation

Test 2: Control of Green Peach Aphid

For evaluating control of green peach aphid (*Myzus persicae*) through systemic means the test unit consisted of 96-well-microtiter plates containing liquid artificial diet under an artificial membrane.

The individual compounds were formulated as a stock-solution containing 75% v/v water and 25% v/v dimethylsulfoxid (DMSO). The stock-solutions were diluted with water to the desired concentrations of the compounds or mixtures and the dilutions were pipetted into the aphid diet, using a custom built pipetter, at two replications. For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23±1° C., 50±5% RH for 3 days. Aphid mortality and fecundity was then visually assessed. For the mixture tested the results are listed in table 2.

TABLE 2

Control of Green Peach Aphid

| | Concentration [ppm] | Oberved Control average [%] | Calculated Control [%] |
|---|---|---|---|
| Compound I | 0.004 | 0 | — |
| Abamectin | 0.016 | 0 | — |
| Abamectin + Compound I | 0.016 + 0.004 | 75* | 0 |
| Bifenthrin | 0.08 | 0 | — |
| Bifenthrin + Compound I | 0.08 + 0.004 | 100* | 0 |

*synergistic control effect according to Colby's equation

Test 3: Control of Boll Weevil

For evaluating control of boll weevil (*Anthonomus grandis*) the test unit consisted of 24-well-microtiter plates containing an insect diet and 20-30 *A. grandis* eggs.

The individual compounds were formulated as a stock-solution containing 75% v/v water and 25% v/v dimethylsulfoxid (DMSO). The stock-solutions were diluted with water to the desired concentrations of the compounds or mixtures and the dilutions were sprayed onto the insect diet at 20 µl, using a custom built micro atomizer, at two replications. For experimental mixtures in these tests identical volumes of both mixing partners at the desired concentrations respectively, were mixed together.

After application, microtiter plates were incubated at 23±1° C., 50±5% RH for 5 days. Egg and larval mortality was then visually assessed. For the mixture tested the results are listed in table 3.

TABLE 3

Control of Boll Weevil

| | Concentration [ppm] | Oberved Control average [%] | Calculated Control [%] |
|---|---|---|---|
| Compound I | 0.02 | 0 | — |
| Compound M26.4 | 2 | 0 | — |
| Compound M26.4 + Compound I | 2 + 0.02 | 50* | 0 |

*synergistic control effect according to Colby's equation
Compound M26.4: 4-{[(6-chloropyrid-3-yl)methyl](2-fluoroethyl)amino}furan-2(5H)-on

The invention claimed is:

1. A mixture comprising
    1) a pesticidal compound of formula I

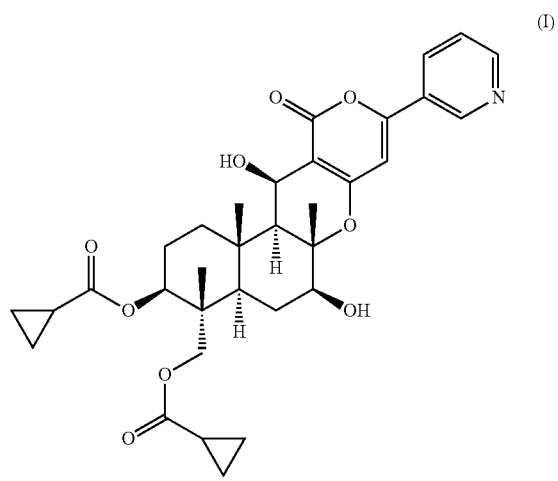

and
    2) one or more pesticidal compounds II selected from:
        a) A pyrethroid compound selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, ethofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;
b) Chloride channel activators selected from the group consisting of abamectin, emamectin benzoate, milbemectin and lepimectin;
c) An aminofuranone compound selected from the group consisting of 4-{[(6-bromopyrid-3-yl)methyl](2-fluoroethyl)amino}furan-2(5H)-on (M26.1), 4-{[(6-fluoropyrid-3-yl)methyl](2,2-difluoroethyl)amino}furan-2(5H)-on (M26.2), 4-{[(2-chloro1,3-thiazolo-5-yl)methyl](2-fluoroethyl)amino}furan-2(5H)-on (M26.3), 4-{[(6-chloropyrid-3-yl)methyl](2-fluoroethyl)amino}furan-2(5H)-on (M26.4), 4-{[(6-chloropyrid-3-yl)methyl](2,2-difluoroethyl)amino}furan-2(5H)-on (M26.5), 4-{[(6-chloro-5-fluoropyrid-3-yl)methyl](methyl)amino}furan-2(5H)-on (M26.6), 4-{[(5,6-dichloropyrid-3-yl)methyl](2-fluoroethyl)amino}furan-2(5H)-on (M26.7), 4-{[(6-chloro-5-fluoropyrid-3-yl)methyl](cyclopropyl)amino}furan-2(5H)-on (M26.8), 4-{[(6-chloropyrid-3-yl)methyl](cyclopropyl)amino}furan-2(5H)-on (M26.9) and 4-{[(6-chloropyrid-3-yl)methyl](methyl)amino}furan-2(5H)-on (M26.10), wherein the ratio by weight of a compound of formula I to the compounds II provides a synergistic pesticidal effect.

2. The mixture according to claim 1, wherein the pesticidal compound II is selected from the group consisting of alpha-cypermethrin, bifenthrin, cypermethrin, deltamethrin, flucythrinate, lambda-cyhalothrin, tefluthrin and permethrin.

3. The mixture according to claim 1, wherein the pesticidal compound II is selected from the group consisting of abamectin, emamectin benzoate, milbemectin and lepimectin.

4. The mixture according to claim 1, wherein the pesticidal compound II is selected from the group consisting of abamectin, bifenthrin, alpha-cypermethrin, and 4-{[(6-chloropyrid-3-yl)methyl](2,2-difluoroethyl)amino}furan-2(5H)-on.

5. The mixture according to claim 1, wherein the pesticidal compound II is selected from the group consisting of bifenthrin, 4-{[(6-chloropyrid-3-yl)methyl](2,2-difluoroethy)amino}furan-2(5H)-on and abamectin.

6. The mixture according to claim 1, wherein the pesticidal compound II is abamectin.

7. The mixture according to claim 1, wherein the pesticidal compound II is bifenthrin.

8. The mixture according to claim 1, wherein the pesticidal compound II is alpha-cypermethrin.

9. The mixture according to claim 1, wherein the pesticidal compound II is 4-{[(6-chloropyrid-3-yl)methyl](2,2-difluoroethyl)amino}furan-2(5H)-one.

10. A method for controlling animal pests, wherein the pest, their habitat, breeding grounds, their locus or the plants to be protected against pest attack, the soil or plant propagation material are treated with an effective amount of the mixture of claim 1.

11. A method for controlling animal pests and/or improving the health of plants, wherein the plant, the locus where the plant is growing or is expected to grow or plant propagation material from which the plant grows are treated with a effective amount the mixture of claim 1.

12. A method for protection of plant propagation material from animal pests comprising contacting the plant propagation materials with the mixture of claim 1 in pesticidally effective amounts.

13. A method as claimed in claim 12, wherein the mixture is applied in an amount of from 0.01 g to 10 kg per 100 kg of plant propagation materials.

14. A method for controlling animal pests, wherein the pest, their habitat, breeding grounds, their locus or the plants to be protected against pest attack, the soil or plant propagation material are treated with an effective amount of
1) a pesticidal compound of formula I

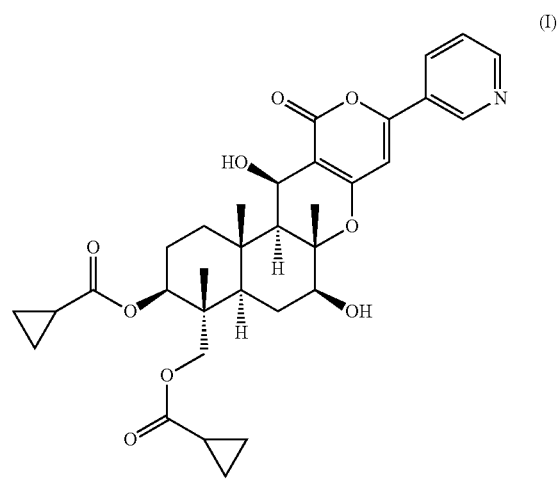

and
2) one or more pesticidal compounds II selected from the compounds of following groups:
a) A pyrethroid compound selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, ethofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;
b) Chloride channel activators selected from the group consisting of abamectin, emamectin benzoate, milbemectin and lepimectin;
c) An aminofuranone compound selected from the group consisting of 4-{[(6-bromopyrid-3-yl)methyl](2-fluoroethyl)amino}furan-2(5H)-on (M26.1), 4-{[(6-fluoropyrid-3-yl)methyl](2,2-difluoroethyl)amino}furan-2(5H)-on (M26.2), 4-{[(2-chloro1,3-thiazolo-5-yl)methyl](2-fluoroethyl)amino}furan-2(5H)-on (M26.3), 4-{[(6-chloropyrid-3-yl)methyl](2-fluoroethyl)amino}furan-2(5H)-on (M26.4), 4-{[(6-chloropyrid-3-yl)methyl](2,2-difluoroethyl)amino}furan-2(5H)-on (M26.5), 4-{[(6-chloro-5-fluoropyrid-3-yl)methyl](methyl)amino}furan-2(5H)-on (M26.6), 4-{[(5,6-dichloropyrid-3-yl)methyl](2-fluoroethyl)amino}furan-2(5H)-on (M26.7), 4-{[(6-chloro-5-fluoropyrid-3-yl)methyl](cyclopropyl)amino}furan-2(5H)-on (M26.8), 4-{[(6-chloropyrid-3-yl)methyl](cyclopropyl)

amino}furan-2(5H)-on (M26.9) and 4-{[(6-chloropyrid-3-yl)methyl](methyl)amino}furan-2 (5H)-on (M26.10),
wherein the compounds are applied simultaneously, that is jointly or separately, or in succession.

15. A method as claimed in claim 10, wherein the animal pests to be controlled are selected from the group of arthropod pests, in particular from insects.

16. Plant propagation material, treated with the mixture of claim 1 in an amount of from 0.01 g to 10 kg per 100 kg of plant propagation materials.

* * * * *